(12) United States Patent
Behnke et al.

(10) Patent No.: US 8,753,334 B2
(45) Date of Patent: Jun. 17, 2014

(54) SYSTEM AND METHOD FOR REDUCING LEAKAGE CURRENT IN AN ELECTROSURGICAL GENERATOR

(75) Inventors: Robert Behnke, Erie, CO (US); David Keppel, Longmont, CO (US)

(73) Assignee: Covidien AG (CH)

( * ) Notice: Subject to any disclaimer, the term of this patent is extended or adjusted under 35 U.S.C. 154(b) by 1650 days.

(21) Appl. No.: 11/431,449

(22) Filed: May 10, 2006

(65) Prior Publication Data
US 2007/0265612 A1   Nov. 15, 2007

(51) Int. Cl.
*A61B 18/12* (2006.01)
*A61B 18/00* (2006.01)

(52) U.S. Cl.
CPC ... *A61B 18/1233* (2013.01); *A61B 2018/00636* (2013.01); *A61B 2018/00702* (2013.01); *A61B 2018/00732* (2013.01); *A61B 2018/00851* (2013.01)
USPC .............................................. 606/34; 606/40

(58) Field of Classification Search
CPC .............. A61B 18/12; A61B 18/1206; A61B 18/1233; A61B 2018/00636; A61B 2018/00702; A61B 2018/00732; A61B 2018/00851
USPC ................................ 606/34, 37–40
See application file for complete search history.

(56) References Cited

U.S. PATENT DOCUMENTS

| | | |
|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 3,058,470 A | 10/1962 | Seeliger et al. |
| 3,089,496 A | 5/1963 | Degelman |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |

(Continued)

FOREIGN PATENT DOCUMENTS

| | | |
|---|---|---|
| DE | 179607 | 3/1905 |
| DE | 1099658 | 2/1961 |

(Continued)

OTHER PUBLICATIONS

International Search Report EP 07008207.8; dated Sep. 5, 2007.

(Continued)

*Primary Examiner* — Michael Peffley
*Assistant Examiner* — Samantha Good

(57) ABSTRACT

A system and method for reducing leakage current in an electrosurgical generator are disclosed. The system includes an electrosurgical generator configured to provide high frequency electrosurgical energy at a fundamental frequency. The generator includes one or more circuit boards having a board ground. The generator further includes a inductor-capacitor filter connected in series with the board ground and an earth ground. The inductor capacitor filter includes a capacitor connected in parallel with an inductor and is tuned to be at an operational frequency which is resonant at or near the fundamental frequency.

11 Claims, 3 Drawing Sheets

(56) References Cited

U.S. PATENT DOCUMENTS

| | | |
|---|---|---|
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,482 A | 10/1973 | Shaw |
| 3,801,766 A | 4/1974 | Morrison, Jr. |
| 3,801,800 A | 4/1974 | Newton |
| 3,801,900 A | 4/1974 | Szasz |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gosner |
| 4,281,373 A | 7/1981 | Mabille |
| 4,287,557 A | 9/1981 | Brehse |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,582,057 A | 4/1986 | Auth et al. |
| 4,586,120 A | 4/1986 | Malik et al. |
| 4,590,934 A | 5/1986 | Malis et al. |
| 4,608,977 A | 9/1986 | Brown |
| 4,615,330 A * | 10/1986 | Nagasaki et al. ............. 600/104 |
| 4,630,218 A | 12/1986 | Hurley |
| 4,632,109 A | 12/1986 | Patterson |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,742,831 A | 5/1988 | Silvian |
| 4,744,364 A | 5/1988 | Kensey |
| 4,754,757 A | 7/1988 | Feucht |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |
| 4,862,889 A | 9/1989 | Feucht |
| 4,887,199 A | 12/1989 | Whittle |
| 4,890,610 A | 1/1990 | Kirwan et al. |
| 4,903,696 A | 2/1990 | Stasz et al. |
| 4,907,589 A | 3/1990 | Cosman |
| 4,922,210 A | 5/1990 | Flachenecker et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,959,606 A | 9/1990 | Forge |
| 4,961,047 A | 10/1990 | Carder |
| 4,961,435 A | 10/1990 | Kitagawa et al. |
| 4,966,597 A | 10/1990 | Cosman |
| 4,969,885 A | 11/1990 | Farin |
| 4,992,719 A | 2/1991 | Harvey |
| 4,993,430 A | 2/1991 | Shimoyama et al. |
| 4,995,877 A | 2/1991 | Ams et al. |
| 5,015,227 A | 5/1991 | Broadwin et al. |

(56) References Cited

U.S. PATENT DOCUMENTS

| | | |
|---|---|---|
| 5,024,668 A | 6/1991 | Peters et al. |
| 5,087,257 A | 2/1992 | Farin |
| 5,099,840 A | 3/1992 | Goble et al. |
| 5,103,804 A | 4/1992 | Abele et al. |
| 5,108,389 A | 4/1992 | Cosmescu |
| 5,108,391 A | 4/1992 | Flachenecker |
| 5,122,137 A | 6/1992 | Lennox |
| 5,133,711 A | 7/1992 | Hagen |
| 5,151,102 A | 9/1992 | Kamiyama et al. |
| 5,152,762 A | 10/1992 | McElhenney |
| 5,157,603 A | 10/1992 | Scheller et al. |
| 5,160,334 A | 11/1992 | Billings et al. |
| 5,167,658 A | 12/1992 | Ensslin |
| 5,174,293 A | 12/1992 | Hagiwara |
| 5,190,517 A | 3/1993 | Zieve et al. |
| 5,196,008 A | 3/1993 | Kuenecke |
| 5,196,009 A | 3/1993 | Kirwan, Jr. |
| 5,201,900 A | 4/1993 | Nardella |
| 5,207,691 A | 5/1993 | Nardella |
| 5,230,623 A | 7/1993 | Guthrie et al. |
| 5,233,515 A | 8/1993 | Cosman |
| 5,249,121 A | 9/1993 | Baum et al. |
| 5,254,117 A | 10/1993 | Rigby et al. |
| RE34,432 E | 11/1993 | Bertrand |
| 5,267,994 A | 12/1993 | Gentelia et al. |
| 5,267,997 A | 12/1993 | Farin |
| 5,281,213 A | 1/1994 | Milder et al. |
| 5,300,068 A | 4/1994 | Rosar et al. |
| 5,300,070 A | 4/1994 | Gentelia |
| 5,318,563 A | 6/1994 | Malis et al. |
| 5,323,778 A | 6/1994 | Kandarpa et al. |
| 5,324,283 A | 6/1994 | Heckele |
| 5,330,518 A | 7/1994 | Neilson et al. |
| 5,334,183 A | 8/1994 | Wuchinich |
| 5,334,193 A | 8/1994 | Nardella |
| 5,341,807 A | 8/1994 | Nardella |
| 5,342,356 A | 8/1994 | Ellman |
| 5,342,357 A | 8/1994 | Nardella |
| 5,342,409 A | 8/1994 | Mullett |
| 5,348,554 A | 9/1994 | Imran et al. |
| 5,370,645 A | 12/1994 | Klicek et al. |
| 5,370,672 A | 12/1994 | Fowler et al. |
| 5,370,675 A | 12/1994 | Edwards et al. |
| 5,372,596 A | 12/1994 | Klicek et al. |
| 5,383,874 A | 1/1995 | Jackson |
| 5,383,876 A | 1/1995 | Nardella |
| 5,383,917 A | 1/1995 | Desai et al. |
| 5,385,148 A | 1/1995 | Lesh et al. |
| 5,395,394 A | 3/1995 | Cameron |
| 5,400,267 A | 3/1995 | Denen et al. |
| 5,403,311 A | 4/1995 | Abele et al. |
| 5,403,312 A | 4/1995 | Yates et al. |
| 5,409,000 A | 4/1995 | Imran |
| 5,409,485 A | 4/1995 | Suda |
| 5,413,573 A | 5/1995 | Koivukangas |
| 5,414,238 A | 5/1995 | Steigerwald et al. |
| 5,417,719 A | 5/1995 | Hull et al. |
| 5,422,567 A | 6/1995 | Matsunaga |
| 5,423,808 A | 6/1995 | Edwards et al. |
| 5,423,809 A | 6/1995 | Klicek |
| 5,423,810 A | 6/1995 | Goble et al. |
| 5,425,704 A | 6/1995 | Sakurai et al. |
| 5,430,434 A | 7/1995 | Lederer et al. |
| 5,432,459 A | 7/1995 | Thompson |
| 5,433,739 A | 7/1995 | Sluijter et al. |
| 5,436,566 A | 7/1995 | Thompson |
| 5,438,302 A | 8/1995 | Goble |
| 5,443,463 A | 8/1995 | Stern et al. |
| 5,445,635 A | 8/1995 | Denen |
| 5,451,224 A | 9/1995 | Goble et al. |
| 5,458,597 A | 10/1995 | Edwards et al. |
| 5,462,521 A | 10/1995 | Brucker et al. |
| 5,472,441 A | 12/1995 | Edwards et al. |
| 5,472,443 A | 12/1995 | Cordis et al. |
| 5,480,399 A | 1/1996 | Hebborn |
| 5,483,952 A | 1/1996 | Aranyi |
| 5,496,312 A | 3/1996 | Klicek |
| 5,496,313 A | 3/1996 | Gentelia et al. |
| 5,500,012 A | 3/1996 | Brucker et al. |
| 5,500,616 A | 3/1996 | Ochi |
| 5,514,129 A | 5/1996 | Smith |
| 5,520,684 A | 5/1996 | Imran |
| 5,531,774 A | 7/1996 | Schulman et al. |
| 5,534,018 A | 7/1996 | Wahlstrand et al. |
| 5,536,267 A | 7/1996 | Edwards et al. |
| 5,540,681 A | 7/1996 | Strul et al. |
| 5,540,683 A | 7/1996 | Ichikawa |
| 5,540,684 A | 7/1996 | Hassler, Jr. |
| 5,556,396 A | 9/1996 | Cohen et al. |
| 5,558,671 A | 9/1996 | Yates |
| 5,569,242 A | 10/1996 | Lax et al. |
| 5,571,147 A | 11/1996 | Sluijter et al. |
| 5,573,533 A | 11/1996 | Strul |
| 5,584,830 A | 12/1996 | Ladd et al. |
| 5,588,432 A | 12/1996 | Crowley |
| 5,596,466 A | 1/1997 | Ochi |
| 5,599,344 A | 2/1997 | Paterson |
| 5,599,345 A | 2/1997 | Edwards et al. |
| 5,599,348 A | 2/1997 | Gentelia et al. |
| 5,605,150 A | 2/1997 | Radons et al. |
| 5,613,966 A | 3/1997 | Makower et al. |
| 5,626,575 A | 5/1997 | Crenner |
| 5,626,631 A | 5/1997 | Eckhouse |
| 5,628,745 A | 5/1997 | Bek |
| 5,643,330 A | 7/1997 | Holsheimer et al. |
| 5,647,869 A | 7/1997 | Goble et al. |
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |
| 5,674,217 A | 10/1997 | Wahlstrom et al. |
| 5,674,266 A | 10/1997 | Stendahl |
| 5,685,840 A | 11/1997 | Schechter et al. |
| 5,688,267 A | 11/1997 | Panescu et al. |
| 5,693,042 A | 12/1997 | Bioarski et al. |
| 5,694,304 A | 12/1997 | Telefus et al. |
| 5,695,494 A | 12/1997 | Becker |
| 5,696,441 A | 12/1997 | Mak et al. |
| 5,702,386 A | 12/1997 | Stern et al. |
| 5,702,429 A | 12/1997 | King |
| 5,707,369 A | 1/1998 | Vaitekunas et al. |
| 5,712,772 A | 1/1998 | Telefus et al. |
| 5,713,896 A | 2/1998 | Nardella |
| 5,718,246 A | 2/1998 | Vona |
| 5,720,744 A | 2/1998 | Eggleston et al. |
| 5,720,772 A | 2/1998 | Eckhouse |
| 5,722,975 A | 3/1998 | Edwards et al. |
| 5,729,448 A | 3/1998 | Haynie et al. |
| 5,733,281 A | 3/1998 | Nardella |
| 5,749,869 A | 5/1998 | Lindenmeier et al. |
| 5,749,871 A | 5/1998 | Hood et al. |
| 5,755,715 A | 5/1998 | Stern |
| 5,755,751 A | 5/1998 | Eckhouse |
| 5,766,165 A | 6/1998 | Gentelia et al. |
| 5,769,847 A | 6/1998 | Panescu |
| 5,772,659 A | 6/1998 | Becker et al. |
| 5,792,138 A | 8/1998 | Shipp |
| 5,797,902 A | 8/1998 | Netherly |
| 5,814,092 A | 9/1998 | King |
| 5,817,093 A | 10/1998 | Williamson, IV et al. |
| 5,820,568 A | 10/1998 | Willis |
| 5,824,016 A | 10/1998 | Ekwall |
| 5,827,271 A | 10/1998 | Bussey et al. |
| 5,830,212 A | 11/1998 | Cartmell |
| 5,836,909 A | 11/1998 | Cosmescu |
| 5,836,943 A | 11/1998 | Miller, III |
| 5,836,990 A | 11/1998 | Li |
| 5,846,236 A | 12/1998 | Lindenmeier et al. |
| 5,860,975 A * | 1/1999 | Goble et al. ............ 606/45 |
| 5,861,006 A | 1/1999 | Kroll |
| 5,868,737 A | 2/1999 | Taylor et al. |
| 5,868,739 A | 2/1999 | Lindenmeier et al. |
| 5,868,740 A | 2/1999 | LeVeen et al. |
| 5,871,481 A | 2/1999 | Kannenberg et al. |

(56) References Cited

U.S. PATENT DOCUMENTS

| | | | |
|---|---|---|---|
| 5,882,312 | A | 3/1999 | Gopakumaran et al. |
| 5,897,552 | A | 4/1999 | Edwards et al. |
| 5,908,444 | A | 6/1999 | Azure |
| 5,913,882 | A | 6/1999 | King |
| 5,921,982 | A | 7/1999 | Lesh et al. |
| 5,925,070 | A | 7/1999 | King et al. |
| 5,931,836 | A | 8/1999 | Hatta et al. |
| 5,938,690 | A | 8/1999 | Law et al. |
| 5,943,633 | A | 8/1999 | Wilson et al. |
| 5,948,007 | A | 9/1999 | Starkenbaum et al. |
| 5,951,545 | A | 9/1999 | Schilling |
| 5,951,546 | A | 9/1999 | Lorentzen |
| 5,954,686 | A | 9/1999 | Garito et al. |
| 5,954,717 | A | 9/1999 | Behl et al. |
| 5,954,719 | A | 9/1999 | Chen et al. |
| 5,961,344 | A | 10/1999 | Rosales et al. |
| 5,971,980 | A | 10/1999 | Sherman |
| 5,976,128 | A | 11/1999 | Schilling et al. |
| 5,983,141 | A | 11/1999 | Sluijter et al. |
| 6,002,957 | A | 12/1999 | Finneran |
| 6,010,499 | A | 1/2000 | Cobb |
| 6,014,581 | A | 1/2000 | Whayne et al. |
| 6,033,399 | A | 3/2000 | Gines |
| 6,041,260 | A * | 3/2000 | Stern et al. .................. 607/98 |
| 6,044,283 | A | 3/2000 | Fein et al. |
| 6,047,202 | A | 4/2000 | Finneran et al. |
| 6,053,910 | A | 4/2000 | Fleenor |
| 6,053,912 | A | 4/2000 | Panescu et al. |
| 6,055,458 | A | 4/2000 | Cochran et al. |
| 6,056,745 | A | 5/2000 | Panescu et al. |
| 6,056,746 | A | 5/2000 | Goble et al. |
| 6,063,075 | A | 5/2000 | Mihori |
| 6,063,078 | A | 5/2000 | Wittkampf |
| 6,068,627 | A | 5/2000 | Orszulak et al. |
| 6,074,386 | A | 6/2000 | Goble et al. |
| 6,074,388 | A | 6/2000 | Tockweiler et al. |
| 6,080,149 | A | 6/2000 | Huang et al. |
| 6,088,608 | A | 7/2000 | Schulman et al. |
| 6,091,987 | A | 7/2000 | Thompson |
| 6,093,186 | A | 7/2000 | Goble |
| 6,102,497 | A | 8/2000 | Ehr et al. |
| 6,113,591 | A | 9/2000 | Whayne et al. |
| 6,113,596 | A | 9/2000 | Hooven |
| 6,123,702 | A | 9/2000 | Swanson et al. |
| 6,132,429 | A | 10/2000 | Baker |
| 6,142,992 | A | 11/2000 | Cheng et al. |
| 6,155,975 | A | 12/2000 | Urich et al. |
| 6,162,217 | A | 12/2000 | Kannenberg et al. |
| 6,167,301 | A | 12/2000 | Flower et al. |
| 6,171,304 | B1 | 1/2001 | Netherly et al. |
| 6,185,458 | B1 | 2/2001 | Ochs et al. |
| 6,185,460 | B1 | 2/2001 | Thompson |
| 6,188,211 | B1 | 2/2001 | Rincon-Mora et al. |
| 6,203,541 | B1 | 3/2001 | Keppel |
| 6,208,896 | B1 | 3/2001 | Mulhauser |
| 6,210,403 | B1 | 4/2001 | Klicek |
| 6,222,356 | B1 | 4/2001 | Taghizadeh-Kaschani |
| 6,228,080 | B1 | 5/2001 | Gines |
| 6,228,081 | B1 | 5/2001 | Goble |
| 6,230,054 | B1 | 5/2001 | Powers |
| 6,231,569 | B1 | 5/2001 | Bek |
| 6,235,020 | B1 | 5/2001 | Cheng et al. |
| 6,236,888 | B1 | 5/2001 | Thompson |
| 6,238,387 | B1 | 5/2001 | Miller, III |
| 6,238,388 | B1 | 5/2001 | Ellman |
| 6,241,725 | B1 | 6/2001 | Cosman |
| 6,245,065 | B1 | 6/2001 | Panescu |
| 6,246,912 | B1 | 6/2001 | Sluijter et al. |
| 6,248,080 | B1 | 6/2001 | Miesel et al. |
| 6,251,106 | B1 | 6/2001 | Becker et al. |
| 6,258,085 | B1 | 7/2001 | Eggleston |
| 6,261,285 | B1 | 7/2001 | Novak |
| 6,261,286 | B1 | 7/2001 | Goble et al. |
| 6,273,886 | B1 | 8/2001 | Edwards |
| 6,275,786 | B1 | 8/2001 | Daners |
| 6,280,438 | B1 | 8/2001 | Eckhouse et al. |
| 6,293,941 | B1 | 9/2001 | Strul |
| 6,293,942 | B1 | 9/2001 | Goble et al. |
| 6,296,636 | B1 | 10/2001 | Cheng et al. |
| 6,306,131 | B1 | 10/2001 | Hareyama et al. |
| 6,306,134 | B1 | 10/2001 | Goble et al. |
| 6,309,386 | B1 | 10/2001 | Bek |
| 6,324,496 | B1 | 11/2001 | Alur et al. |
| 6,325,799 | B1 | 12/2001 | Goble |
| 6,337,998 | B1 | 1/2002 | Behl et al. |
| 6,338,657 | B1 | 1/2002 | Harper et al. |
| 6,350,262 | B1 | 2/2002 | Ashley |
| 6,358,245 | B1 | 3/2002 | Edwards |
| 6,364,877 | B1 | 4/2002 | Goble et al. |
| 6,383,183 | B1 | 5/2002 | Sekino et al. |
| 6,387,048 | B1 | 5/2002 | Schulman et al. |
| 6,390,972 | B1 | 5/2002 | Speier et al. |
| 6,391,024 | B1 | 5/2002 | Sun et al. |
| 6,398,779 | B1 | 6/2002 | Buysse et al. |
| 6,398,781 | B1 | 6/2002 | Goble et al. |
| 6,402,732 | B1 | 6/2002 | Flower et al. |
| 6,402,741 | B1 | 6/2002 | Keppel et al. |
| 6,402,743 | B1 | 6/2002 | Orszulak et al. |
| 6,416,509 | B1 | 7/2002 | Goble et al. |
| 6,418,342 | B1 | 7/2002 | Owen et al. |
| 6,436,096 | B1 | 8/2002 | Hareyama |
| 6,451,015 | B1 | 9/2002 | Rittman, III et al. |
| 6,458,121 | B1 | 10/2002 | Rosenstock |
| 6,464,689 | B1 | 10/2002 | Qin |
| 6,464,696 | B1 | 10/2002 | Oyama |
| 6,498,466 | B1 | 12/2002 | Edwards |
| 6,506,189 | B1 | 1/2003 | Rittman, III et al. |
| 6,508,815 | B1 | 1/2003 | Strul |
| 6,511,476 | B2 | 1/2003 | Hareyama |
| 6,511,478 | B1 | 1/2003 | Burnside et al. |
| 6,514,243 | B1 | 2/2003 | Eckhouse et al. |
| 6,517,538 | B1 | 2/2003 | Jacob et al. |
| 6,522,919 | B1 | 2/2003 | Flower et al. |
| 6,524,308 | B1 | 2/2003 | Muller et al. |
| 6,546,285 | B1 | 4/2003 | Owen et al. |
| 6,547,786 | B1 | 4/2003 | Goble |
| 6,558,376 | B2 | 5/2003 | Bishop |
| 6,560,470 | B1 | 5/2003 | Pologe |
| 6,562,037 | B2 | 5/2003 | Paton |
| 6,565,559 | B2 | 5/2003 | Eggleston |
| 6,575,969 | B1 | 6/2003 | Rittman, III et al. |
| 6,582,427 | B1 | 6/2003 | Goble et al. |
| 6,620,157 | B1 | 9/2003 | Dabney et al. |
| 6,623,423 | B2 | 9/2003 | Sakurai |
| 6,629,973 | B1 | 10/2003 | Wardell et al. |
| 6,635,057 | B2 | 10/2003 | Harano |
| 6,636,010 | B1 | 10/2003 | Malmstrom et al. |
| 6,645,198 | B1 | 11/2003 | Bommannan et al. |
| 6,648,883 | B2 | 11/2003 | Francischelli |
| 6,652,514 | B2 | 11/2003 | Ellman |
| 6,663,623 | B1 | 12/2003 | Oyama et al. |
| 6,663,624 | B2 | 12/2003 | Edwards |
| 6,666,860 | B1 | 12/2003 | Takahashi |
| 6,671,545 | B2 | 12/2003 | Fincke |
| 6,679,875 | B2 | 1/2004 | Honda |
| 6,682,527 | B2 | 1/2004 | Strul |
| 6,685,700 | B2 | 2/2004 | Behl |
| 6,685,701 | B2 | 2/2004 | Orszulak et al. |
| 6,685,703 | B2 | 2/2004 | Pearson et al. |
| 6,689,131 | B2 | 2/2004 | McClurken |
| 6,692,489 | B1 | 2/2004 | Heim |
| 6,693,782 | B1 | 2/2004 | Lash |
| 6,712,813 | B2 | 3/2004 | Ellman |
| 6,730,080 | B2 | 5/2004 | Harano |
| 6,733,495 | B1 | 5/2004 | Bek |
| 6,733,498 | B2 | 5/2004 | Paton |
| 6,740,079 | B1 | 5/2004 | Eggers |
| 6,740,085 | B2 | 5/2004 | Hareyama |
| 6,745,062 | B1 | 6/2004 | Finneran et al. |
| 6,755,825 | B2 | 6/2004 | Shoenman et al. |
| 6,758,846 | B2 | 7/2004 | Goble et al. |
| 6,783,523 | B2 | 8/2004 | Qin |
| 6,786,905 | B2 | 9/2004 | Swanson et al. |
| 6,790,206 | B2 | 9/2004 | Panescu |

(56) References Cited

U.S. PATENT DOCUMENTS

| | | |
|---|---|---|
| 6,796,981 B2 | 9/2004 | Wham |
| 6,824,539 B2 | 11/2004 | Novak |
| 6,830,569 B2 | 12/2004 | Thompson |
| 6,843,789 B2 | 1/2005 | Goble |
| 6,849,073 B2 | 2/2005 | Hoey |
| 6,855,141 B2 | 2/2005 | Lovewell |
| 6,855,142 B2 | 2/2005 | Harano |
| 6,860,881 B2 | 3/2005 | Sturm |
| 6,864,686 B2 | 3/2005 | Novak |
| 6,875,210 B2 | 4/2005 | Refior |
| 6,893,435 B2 | 5/2005 | Goble |
| 6,923,804 B2 | 8/2005 | Eggers et al. |
| 6,929,641 B2 | 8/2005 | Goble et al. |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,966,907 B2 | 11/2005 | Goble |
| 6,989,010 B2 | 1/2006 | Francischelli et al. |
| 6,994,704 B2 | 2/2006 | Qin et al. |
| 6,994,707 B2 | 2/2006 | Ellman et al. |
| 7,001,381 B2 | 2/2006 | Harano et al. |
| 7,004,174 B2 | 2/2006 | Eggers et al. |
| 7,041,096 B2 | 5/2006 | Malis et al. |
| 7,044,948 B2 | 5/2006 | Keppel |
| 7,044,949 B2 | 5/2006 | Orszulak et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,122,031 B2 | 10/2006 | Edwards et al. |
| 7,131,860 B2 | 11/2006 | Sartor et al. |
| 7,137,980 B2 | 11/2006 | Buysse et al. |
| 7,147,638 B2 | 12/2006 | Chapman et al. |
| 7,160,293 B2 | 1/2007 | Sturm et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,211,081 B2 | 5/2007 | Goble |
| 7,214,224 B2 | 5/2007 | Goble |
| 7,220,260 B2 | 5/2007 | Fleming et al. |
| 7,247,155 B2 | 7/2007 | Hoey et al. |
| 7,250,746 B2 | 7/2007 | Oswald et al. |
| 7,255,694 B2 | 8/2007 | Keppel |
| 7,282,048 B2 | 10/2007 | Goble et al. |
| 7,300,435 B2 | 11/2007 | Wham et al. |
| 7,303,557 B2 | 12/2007 | Wham et al. |
| 7,364,577 B2 | 4/2008 | Wham et al. |
| 7,367,972 B2 | 5/2008 | Francischelli et al. |
| RE40,388 E | 6/2008 | Gines |
| 7,396,336 B2 | 7/2008 | Orszulak et al. |
| 2001/0014804 A1 | 8/2001 | Goble et al. |
| 2001/0029315 A1 | 10/2001 | Sakurai et al. |
| 2001/0031962 A1 | 10/2001 | Eggleston |
| 2002/0035363 A1 | 3/2002 | Edwards et al. |
| 2002/0035364 A1 | 3/2002 | Schoenman et al. |
| 2002/0042561 A1 | 4/2002 | Schulman et al. |
| 2002/0052599 A1 | 5/2002 | Goble |
| 2002/0068932 A1 | 6/2002 | Edwards |
| 2002/0072770 A1 | 6/2002 | Pless |
| 2002/0107517 A1 | 8/2002 | Witt et al. |
| 2002/0111624 A1 | 8/2002 | Witt et al. |
| 2002/0151889 A1 | 10/2002 | Swanson et al. |
| 2002/0193787 A1 | 12/2002 | Qin |
| 2003/0004510 A1 | 1/2003 | Wham et al. |
| 2003/0009102 A1 | 1/2003 | Quistgaard et al. |
| 2003/0060818 A1 | 3/2003 | Kannenberg |
| 2003/0069567 A1 | 4/2003 | Eckhouse et al. |
| 2003/0074025 A1 | 4/2003 | Wuthrich |
| 2003/0078572 A1 | 4/2003 | Pearson et al. |
| 2003/0083724 A1 | 5/2003 | Jog et al. |
| 2003/0087197 A1 | 5/2003 | Schulman et al. |
| 2003/0139741 A1 | 7/2003 | Goble et al. |
| 2003/0153908 A1 | 8/2003 | Goble |
| 2003/0163123 A1 | 8/2003 | Goble |
| 2003/0163124 A1 | 8/2003 | Goble |
| 2003/0171745 A1 | 9/2003 | Francischelli |
| 2003/0181898 A1* | 9/2003 | Bowers ........................... 606/34 |
| 2003/0199863 A1 | 10/2003 | Swanson |
| 2003/0225401 A1 | 12/2003 | Eggers et al. |
| 2004/0002745 A1 | 1/2004 | Flemming |
| 2004/0015159 A1 | 1/2004 | Slater et al. |
| 2004/0015163 A1 | 1/2004 | Buysse et al. |
| 2004/0015216 A1 | 1/2004 | DeSisto |
| 2004/0019347 A1 | 1/2004 | Sakurai |
| 2004/0024395 A1 | 2/2004 | Ellman |
| 2004/0030328 A1 | 2/2004 | Eggers |
| 2004/0030330 A1 | 2/2004 | Brassell et al. |
| 2004/0044339 A1 | 3/2004 | Beller |
| 2004/0049179 A1 | 3/2004 | Francischelli |
| 2004/0054365 A1 | 3/2004 | Goble |
| 2004/0059323 A1 | 3/2004 | Sturm et al. |
| 2004/0068304 A1 | 4/2004 | Paton |
| 2004/0082946 A1 | 4/2004 | Malis |
| 2004/0095100 A1 | 5/2004 | Thompson |
| 2004/0097912 A1 | 5/2004 | Gonnering |
| 2004/0097914 A1 | 5/2004 | Pantera et al. |
| 2004/0097915 A1 | 5/2004 | Refior |
| 2004/0116918 A1 | 6/2004 | Konesky |
| 2004/0116919 A1 | 6/2004 | Heim |
| 2004/0133189 A1 | 7/2004 | Sakurai |
| 2004/0138653 A1 | 7/2004 | Dabney et al. |
| 2004/0138654 A1 | 7/2004 | Goble |
| 2004/0143263 A1 | 7/2004 | Schechter et al. |
| 2004/0147918 A1 | 7/2004 | Keppel |
| 2004/0152996 A1 | 8/2004 | Gersing |
| 2004/0167508 A1 | 8/2004 | Wham et al. |
| 2004/0172016 A1 | 9/2004 | Bek |
| 2004/0193148 A1 | 9/2004 | Wham et al. |
| 2004/0230189 A1 | 11/2004 | Keppel |
| 2004/0243120 A1 | 12/2004 | Orszulak et al. |
| 2004/0260279 A1 | 12/2004 | Goble |
| 2004/0260354 A1 | 12/2004 | Nielsen et al. |
| 2004/0267134 A1 | 12/2004 | Hossack et al. |
| 2005/0004564 A1 | 1/2005 | Wham |
| 2005/0004569 A1 | 1/2005 | Witt et al. |
| 2005/0004621 A1 | 1/2005 | Boveja et al. |
| 2005/0020889 A1 | 1/2005 | Garboski et al. |
| 2005/0021020 A1 | 1/2005 | Blaha et al. |
| 2005/0021022 A1 | 1/2005 | Sturm et al. |
| 2005/0049655 A1 | 3/2005 | Boveja et al. |
| 2005/0101949 A1 | 5/2005 | Harano et al. |
| 2005/0101951 A1 | 5/2005 | Wham |
| 2005/0113818 A1 | 5/2005 | Sartor |
| 2005/0113819 A1 | 5/2005 | Wham |
| 2005/0149151 A1 | 7/2005 | Orszulak |
| 2005/0182398 A1 | 8/2005 | Paterson |
| 2005/0197659 A1 | 9/2005 | Bahney |
| 2005/0203504 A1 | 9/2005 | Wham et al. |
| 2006/0025760 A1 | 2/2006 | Podhajsky |
| 2006/0079871 A1 | 4/2006 | Plaven et al. |
| 2006/0161148 A1 | 7/2006 | Behnke |
| 2006/0178664 A1 | 8/2006 | Keppel |
| 2006/0224152 A1 | 10/2006 | Behnke et al. |
| 2006/0281360 A1 | 12/2006 | Sartor et al. |
| 2007/0038209 A1 | 2/2007 | Buysse et al. |
| 2007/0093800 A1 | 4/2007 | Wham et al. |
| 2007/0093801 A1 | 4/2007 | Behnke |
| 2007/0135812 A1 | 6/2007 | Sartor |
| 2007/0173802 A1 | 7/2007 | Keppel |
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2007/0173806 A1 | 7/2007 | Orszulak et al. |
| 2007/0173810 A1 | 7/2007 | Orszulak |
| 2007/0173813 A1 | 7/2007 | Odom |
| 2007/0208339 A1 | 9/2007 | Arts et al. |
| 2007/0225698 A1 | 9/2007 | Orszulak et al. |
| 2007/0250052 A1 | 10/2007 | Wham |
| 2007/0265612 A1 | 11/2007 | Behnke et al. |
| 2007/0282320 A1 | 12/2007 | Buysse et al. |
| 2008/0015564 A1 | 1/2008 | Wham et al. |
| 2008/0039831 A1 | 2/2008 | Odom et al. |

(56) References Cited

U.S. PATENT DOCUMENTS

| | | | |
|---|---|---|---|
| 2008/0039836 A1 | 2/2008 | Odom et al. | |
| 2008/0082094 A1 | 4/2008 | McPherson et al. | |
| 2008/0125767 A1 | 5/2008 | Blaha | |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 A1 | 5/1995 |
| DE | 19717411 | 11/1998 |
| DE | 19848540 A1 | 5/2000 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 0569130 A1 | 11/1993 |
| EP | 608609 | 8/1994 |
| EP | 0694291 | 1/1996 |
| EP | 836868 | 4/1998 |
| EP | 878169 | 11/1998 |
| EP | 1051948 | 11/2000 |
| EP | 1053720 | 11/2000 |
| EP | 1151725 | 11/2001 |
| EP | 1293171 | 3/2003 |
| EP | 1472984 | 11/2004 |
| EP | 1495712 | 1/2005 |
| EP | 1500378 | 1/2005 |
| EP | 1535581 | 6/2005 |
| EP | 1609430 | 12/2005 |
| EP | 1645235 | 4/2006 |
| EP | 0880220 B1 | 6/2006 |
| EP | 1707143 | 10/2006 |
| EP | 1810628 | 7/2007 |
| EP | 1810630 | 7/2007 |
| EP | 1810633 | 7/2007 |
| FR | 1275415 | 10/1961 |
| FR | 1347865 | 11/1963 |
| FR | 2313708 | 12/1976 |
| FR | 2502935 | 10/1982 |
| FR | 2517953 | 6/1983 |
| FR | 2573301 | 5/1986 |
| GB | 607850 | 9/1948 |
| GB | 855459 | 11/1960 |
| GB | 902775 | 8/1962 |
| GB | 2164473 | 3/1986 |
| GB | 2214430 | 9/1989 |
| GB | 2358934 A | 8/2001 |
| SU | 166452 | 1/1965 |
| SU | 727201 | 4/1980 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39086 | 12/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/11648 | 4/1997 |
| WO | WO97/17029 | 5/1997 |
| WO | WO02/11634 | 2/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO03/090630 | 11/2003 |
| WO | WO03/090635 | 11/2003 |
| WO | WO03/092520 | 11/2003 |
| WO | WO2004/028385 | 4/2004 |
| WO | WO2004/098385 | 4/2004 |
| WO | WO2004/103156 | 12/2004 |
| WO | WO2005/046496 | 5/2005 |
| WO | WO2005/048809 | 6/2005 |
| WO | WO2005/050151 | 6/2005 |
| WO | WO2005048809 A1 | 6/2005 |
| WO | WO2005/060365 | 7/2005 |
| WO | WO2005/060849 | 7/2005 |

OTHER PUBLICATIONS

International Search Report EP 07010673.7; dated Sep. 24, 2007.
International Search Report EP 06000708.5 dated Apr. 21, 2006.
International Search Report—Extended EP 06000708.5 dated Aug. 22, 2006.
International Search Report EP 05002769.7 dated Jun. 9, 2006.
International Search Report EP 06006717.0 dated Aug. 7, 2006.
Ni W et al: "A Signal Processing Method for the Coriolis Mass Flowmeter Based on a Normalized . . . " Journal of Applied Sciences—Yingyong Kexue Xuebao, Shanghai CN, vol. 23 No. 2;(Mar. 2005); 160-164.
International Search Report EP 07009322.4; dated Dec. 19, 2007.
International Search Report EP06022028.2 dated Feb. 5, 2007.
International Search Report EP06025700.3 dated Apr. 12, 2007.
International Search Report EP07001481.6 dated Apr. 23, 2007.
International Search Report EP07001485.7 dated May 15, 2007.
International Search Report EP07001527.6 dated May 9, 2007.
International Search Report EP07004355.9 dated May 21, 2007.
Muller et al., "Extended Left Hemicolectomy Using the LigaSure Vessel Sealing System" Innovations That Work; Sep. 1999.
International Search Report EP 06010499.9 dated Jan. 29, 2008.
International Search Report EP 07001489.9 dated Dec. 20, 2007.
International Search Report EP 07001491 dated Jun. 6, 2007.
International Search Report EP 07009322.4 dated Jan. 14, 2008.
International Search Report EP 07015601.3 dated Jan. 4, 2008.
International Search Report EP 07015602.1 dated Dec. 20, 2007.
International Search Report EP 07019174.7 dated Jan. 29, 2008.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Anderson et al., "A Numerical Study of Rapid Heating for High Temperature Radio Frequency Hyperthermia" International Journal of Bio-Medical Computing. 35 (1994) pp. 297-307.
Astrahan, "A Localized Current Field Hyperthermia System for Use with 192-Iridium Interstitial Implants" Medical Physics, 9 (3), May/Jun. 1982.
Bergdahl et al., "Studies on Coagulation and the Development of an Automatic Computerized Bipolar Coagulator" Journal of Neurosurgery 75:1, (Jul. 1991) pp. 148-151.
Chicharo at al. "A Sliding Goertzel Algorith" Aug. 1996, pp. 283-297 Signal Processing, Elsevier Science Publishers B.V. Amsterdam, NL vol. 52 No. 3.

(56) References Cited

OTHER PUBLICATIONS

Cosman et al., "Methods of Making Nervous System Lesions" In William RH, Rengachary SS (eds): Neurosurgery, New York: McGraw-Hill, vol. 111, (1984), pp. 2490-2499.

Cosman et al., "Radiofrequency Lesion Generation and Its Effect on Tissue Impedance" Applied Neurophysiology 51: (1988) pp. 230-242.

Cosman et al., "Theoretical Aspects of Radiofrequency Lesions in the Dorsal Root Entry Zone" Neurosurgery 15:(1984) pp. 945-950.

Geddes et al., "The Measurement of Physiologic Events by Electrical Impedence" Am. J. MI, Jan. Mar. 1964, pp. 16-27.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure "The O.R. Pro 300" 1 p. Sep. 1998.

Ogden Goertzel Alternative to the Fourier Transform: Jun. 1993 pp. 485-487 Electronics World; Reed Business Publishing, Sutton, Surrey, BG vol. 99, No. 9. 1687.

Sugita et al., "Bipolar Coagulator with Automatic Thermocontrol" J. Neurosurg., vol. 41, Dec. 1944, pp. 777-779.

Valleylab Brochure "Valleylab Electroshield Monitoring System" 2 pp. Nov. 1995.

Vallfors et al., "Automatically Controlled Bipolar Electrosoagulation-'COA-COMP'" Neurosurgical Review 7:2-3 (1984) pp. 187-190.

Wald et al., "Accidental Burns" JAMA, Aug. 16, 1971, vol. 217, No. 7, pp. 916-921.

Richard Wolf Medical Instruments Corp. Brochure, "Kleppinger Bipolar Forceps & Bipolar Generator" 3 pp. Jan. 1989.

International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.

* cited by examiner

SYSTEM AND METHOD FOR REDUCING LEAKAGE CURRENT IN AN ELECTROSURGICAL GENERATOR

BACKGROUND

1. Technical Field

The present disclosure relates to an electrosurgical system and method. More particularly, the present disclosure relates to a system and method for reducing the risk of alternate site tissue damage by reducing the overall leakage current in the electrosurgical system.

2. Background of Related Art

Electrosurgery involves application of high radio frequency electrical current to a surgical site to cut, ablate, or coagulate tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact of body tissue with either of the separated electrodes does not cause current to flow.

Tissue damage may occur when either the ground or return cable connecting the return electrode plates to the RF source is broken or the patient moves out of contact with the return electrode. When either of these conditions occur and there is also another or secondary ground contact to the patient, current will flow through the secondary ground contact and cause localized tissue damage to the patient at the point where the secondary ground contacts the patient. Such secondary ground may be created by monitoring electrodes connected to the patient, grounded adjacent metallic equipment, etc. In other words, when the normal ground return is broken or separated from the patient, the electrical energy flowing through the active electrode seeks alternate current paths if they exist. Because these other paths usually contact the patient over small areas, the current densities may be very high, which may result in tissue damage.

Conventional electrosurgical generators isolate the RF output by use of a transformer. The capacitive coupling of this transformer controls the amount of leakage current that flows from the RF output to the ground contact and back to the generator. However, since only the transformer is used to isolate the output, the leakage current may have an alternate path to the internal board grounds of the generator and may, therefore, cause tissue damage.

SUMMARY

The present disclosure relates to an electrosurgical generator configured to minimize the flow of leakage current. In particular, the generator is configured to output electrosurgical high frequency energy at a fundamental frequency and includes one or more circuit boards comprising electronic components of the generator, such as an RF output stage. The circuit board includes a board ground that is connected in series with a parallel inductor-capacitor filter. The inductor-capacitor filter is tuned to be resonant at or near the fundamental output frequency of the generator, thereby blocking the flow of leakage current and causing the leakage current to flow back into the generator.

According to one aspect of the present disclosure, an electrosurgical generator configured to provide high frequency electrosurgical energy at a fundamental frequency is disclosed. The generator includes one or more circuit boards having a board ground. The generator further includes a inductor-capacitor filter connected in series with the board ground. The inductor capacitor filter includes a capacitor connected in parallel with an inductor and is tuned to be at an operational frequency, which is resonant at or near the fundamental frequency.

According to another aspect of the present disclosure, an electrosurgical circuit board is disclosed. The circuit board includes an RF output stage that generates sinusoidal waveforms of high frequency electrosurgical energy at a fundamental frequency for one or more electrosurgical modes. The circuit board also includes a board ground and a inductor-capacitor filter connected in series with the board ground. The inductor capacitor filter includes a capacitor connected in parallel with an inductor and is tuned to be at an operational frequency, which is resonant at or near fundamental frequency.

According to a further aspect of the present disclosure, a method for reducing leakage current in an electrosurgical generator is disclosed. The method includes the steps of providing one or more circuit boards having a board ground and connecting a inductor-capacitor filter in series with the board ground. The inductor-capacitor filter includes a capacitor connected in parallel with an inductor and is tuned to be at an operational frequency, which is resonant at or near the fundamental frequency.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail. Those skilled in the art will understand that the invention according to the present disclosure may be adapted for use with either monopolar or bipolar electrosurgical systems.

Figure 1:
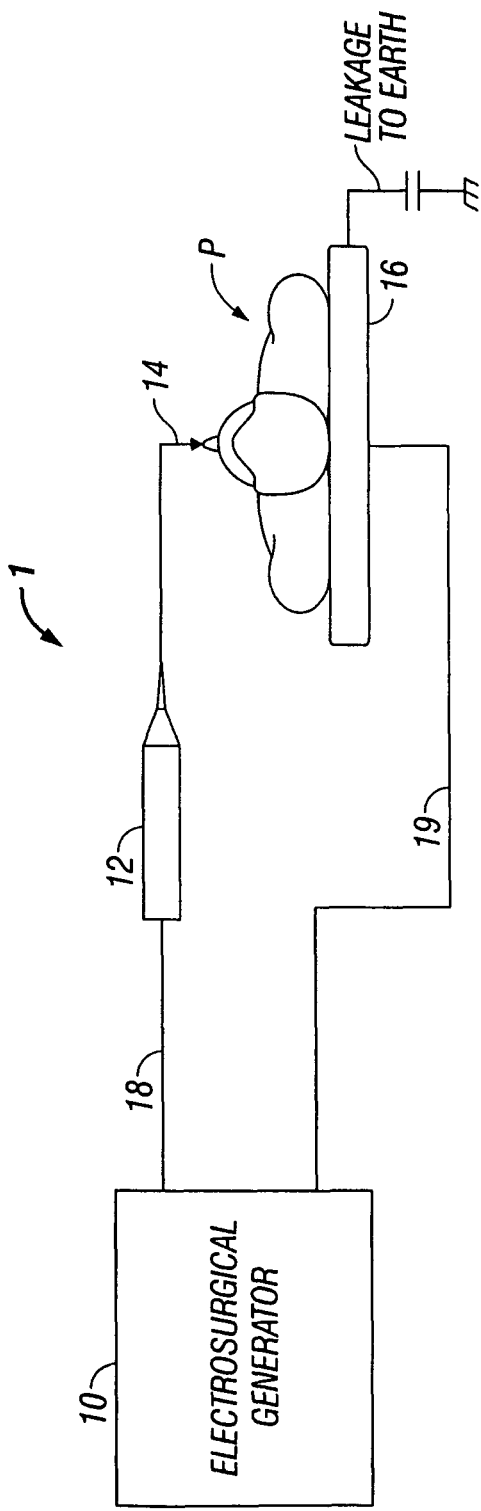
FIG. 1 is a schematic block diagram of an electrosurgical system according to the present disclosure.

FIG. 1 is a schematic illustration of an electrosurgical system including a leakage path to earth ground. The system 1 is a monopolar electrosurgical system that includes an electrosurgical instrument 10 having one or more electrodes for treating tissue of a patient P. The system includes an electrosurgical generator 10 that supplies electrosurgical radio frequency ("RF") energy to a monopolar instrument 12 having an active electrode 14. Electrosurgical RF energy is supplied to the active electrode 14 by a generator 10 via a supply line 18, which is connected to an active output terminal allowing the active electrode 14 to coagulate, seal and/or otherwise treat tissue. The RF energy is returned to the generator 10 via a return electrode 16 (shown as a return pad) via a return transmission line 19, which is connected to a return output terminal. There is leakage to earth ground from the return electrode 16.

System 1 may include a plurality of return electrodes 16 which is believed to minimize the chances of damaged tissue by maximizing the overall contact area with the patient P. In addition, the generator 2 and the return electrode 16 may be configured for monitoring so called "tissue-to-patient" contact to insure that sufficient contact exists therebetween to further minimize chances of tissue damage. The generator 2 may also include a plurality of supply and return terminals and corresponding number of transmission cables (e.g., two of each).

The generator 10 includes suitable input controls (e.g., buttons, activators, switches, touch screen, etc.) for controlling the generator 10. In addition, the generator 10 may include one or more display screens for providing the surgeon with variety of suitable output information (e.g., intensity settings, treatment complete indicators, etc.). The controls allow the surgeon to adjust power of the RF energy, select the waveform, and modify other parameters to achieve the desired waveform suitable for a particular task (e.g., coagulating, tissue sealing, intensity setting, etc.). Disposed between the generator 10 and the active electrode 14 on the supply line 18 is the monopolar instrument 12, which includes a plurality of input controls that may be redundant with certain input controls of the generator 10. Placing the input controls at the hand piece 12 allows for easier and faster modification of RF energy parameters during the surgical procedure without requiring interaction with the generator 10. A footswitch may also be connected to the generator 10 to control energy delivery during monopolar procedures.

Figure 2:
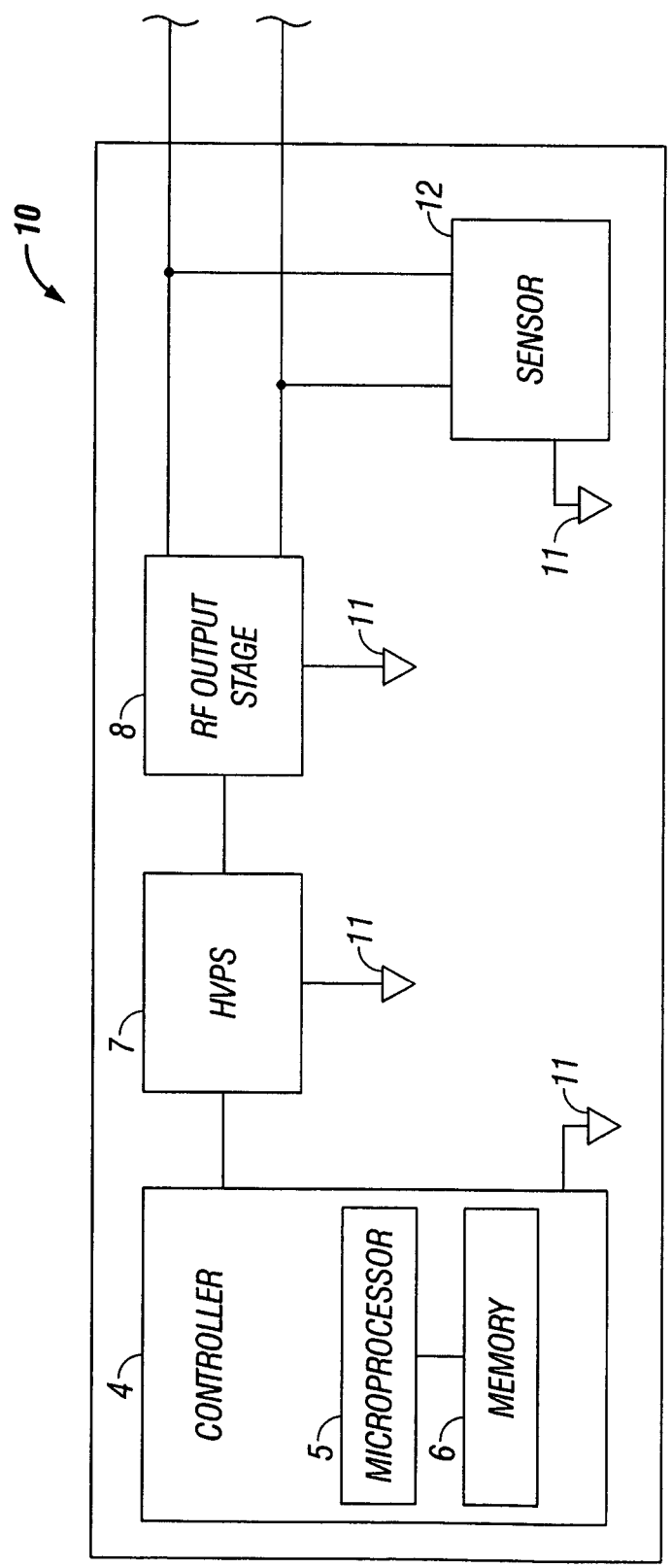
FIG. 2 is a schematic block diagram of a generator according to the present disclosure.
Figure 3:
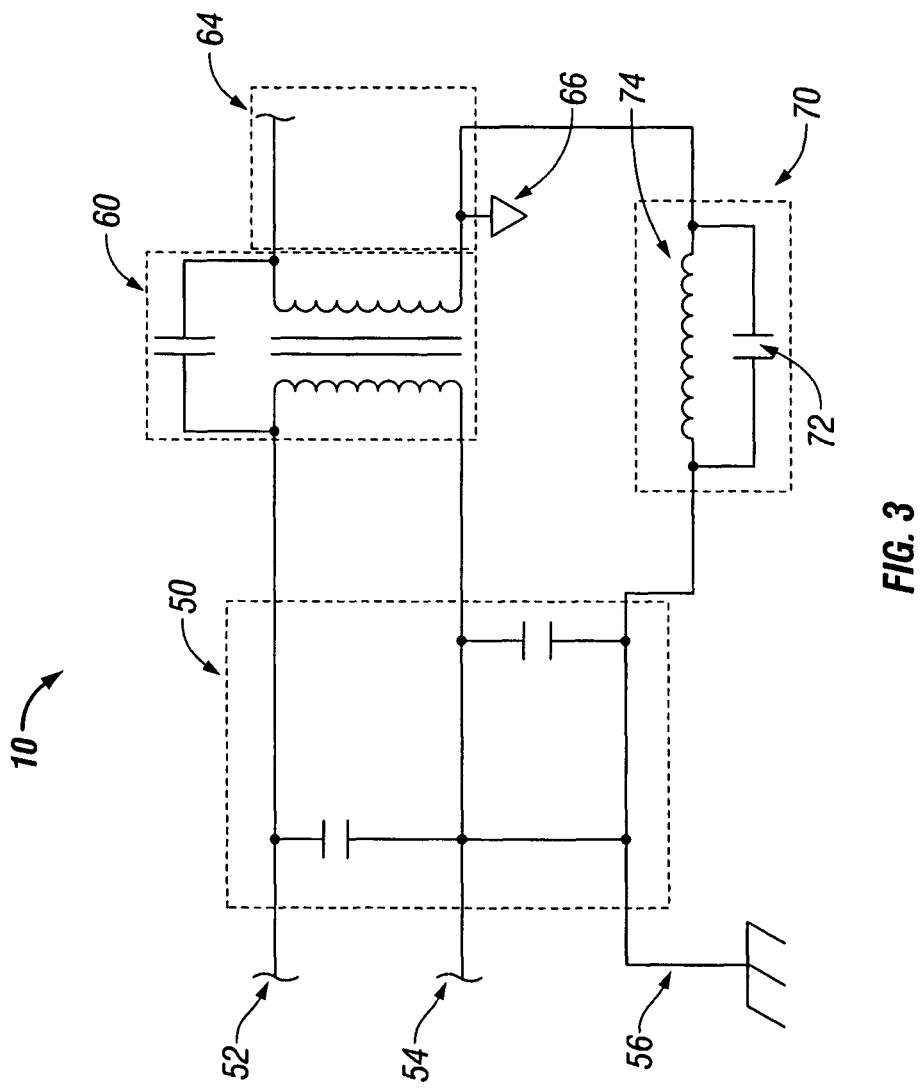
FIG. 3 is a schematic circuit diagram of the electrosurgical generator of FIG. 2.

FIG. 2 shows a schematic block diagram of the generator 10 having a controller 4, a high voltage DC power supply 7 ("HVPS") and an RF output stage 8 all referenced to a ground 11. The ground 11 is not shorted to earth ground and is instead isolated by an LC filter 70 as shown in FIG. 3 at the operating frequency of the generator. The HVPS 7 provides high voltage DC power to an RF output stage 8, which then converts high voltage DC power into RF energy and delivers the RF energy to the active electrode 14. In particular, the RF output stage 8 generates sinusoidal waveforms of high frequency RF energy. The RF output stage 8 is configured to generate a plurality of waveforms having various duty cycles, peak voltages, crest factors, and other suitable parameters. Certain types of waveforms are suitable for specific electrosurgical modes. For instance, the RF output stage 8 generates a 100% duty cycle sinusoidal waveform in cut mode, which is best suited for dissecting tissue and a 25% duty cycle waveform in coagulation mode, which is best used for cauterizing tissue to stop bleeding.

The controller 4 includes a microprocessor 5 connected to a memory 6, which may be volatile type memory (e.g., RAM) and/or non-volatile type memory (e.g., flash media, disk media, etc.). The microprocessor 5 includes an output port that is connected to the HVPS 7 and/or RF output stage 8 allowing the microprocessor 5 to control the output of the generator 10 according to either open and/or closed control loop schemes. A closed loop control scheme may be a feedback control loop wherein the sensor circuitry 11, which may include a plurality of sensing mechanisms (e.g., tissue impedance, tissue temperature, output current and/or voltage, etc.), provides feedback to the controller 4. The controller 4 then signals the HVPS 7 and/or RF output stage 8, which then adjusts DC and/or RF power supply, respectively. The controller 4 also receives input signals from the input controls of the generator 10 and the instrument 12. The controller 4 utilizes the input signals to adjust power outputted by the generator 10 and/or performs other suitable control functions thereon.

FIG. 3 shows a circuit schematic of the generator 10. The generator 10 is connected through an AC line 50 to an electrical outlet providing AC power. The AC line 50 includes three contacts: a line contact 52; a neutral contact 54; and an earth ground contact 56. The AC power is provided to a DC power supply 60, which includes a low voltage power supply (not explicitly shown) and the HVPS 7. The low voltage power supply provides power to various components of the generator (e.g., input controls, displays, etc.). The DC power supply 60 converts AC power into corresponding low and high voltage DC power.

The generator 10 further includes at least one circuit board 64 on which the components of the generator 10 are disposed (e.g., RF output stage 8). The circuit board 64 includes a board ground 66 that grounds to chassis of the generator 10 (e.g., casing) or the earth ground contact 56. In addition, an inductor-capacitor (LC) filter 70 is connected in series with the board ground 66 to the earth ground 56. The LC filter 70 includes a capacitor 72 connected in parallel with an inductor 74 and is tuned to an operational frequency making the LC filter 70 resonant at or near the fundamental frequency of the generator 10. The inductor 74 in the LC filter 70 is tuned to resonate with the capacitance of the AC line 50, the transformer capacitance of the DC power supply 60 and the capacitor 72 at or near the fundamental frequency of the generator 10. This denotes the frequency at which the RF output stage 8 produces electrosurgical waveforms. The fundamental frequency of the generator 10 is about 472 kHz, and may be from about 100 kHz to 3.3 MHz. The LC filter 70 creates a high impedance at the resonant frequency, which allows current at the frequencies below or above the fundamental frequency, to pass through the filter. This allows current at the frequencies other than the fundamental frequencies, e.g., DC current, to be shunted into the earth ground 56. The current at the fundamental frequency flows back to the generator 10, in particular, the circuit board 64 and the board ground 66. This, in turn, reduces the amount of leakage current flowing through the system 1. This resonance creates a high impedance between the earth ground 56 and the board ground 66. Consequently, the board ground 66 is the main path for high frequency leakage current to flow from the earth ground 56 back to the RF output stage 8. By placing a high resistance load between the earth ground 56 and the board ground 66 the RF output stage 8 is further isolated from the earth ground 56 thereby further reducing high frequency leakage.

The amount of leakage current of the generator is expressed by the following formula (1):

$$I_{leak} = 2 * \pi * f * V * C \quad (1)$$

In formula (1), $f$ is the fundamental frequency, V is the output voltage in rms, C is the capacitive coupling between the output and the earth ground contact 56. There is a limit as to the amount the capacitive coupling may be reduced in order to reduce the $I_{leak}$. To limit the leakage current any further, the generator 10 needs to be isolated from the earth ground contact 56. Simply removing the earth ground contact 56 from the board ground 66 is insufficient due to the natural capacitance of the AC power input (e.g., through the AC line 50) from the earth ground contact 56 to the board ground 66. The LC filter 70 takes this capacitance C into account and uses it to resonate at the fundamental output frequency in the manner discussed above to reduce the amount of leakage current. In particular, the LC filter 70 causes the leakage current at the fundamental frequency to flow back to the generator 10.

While several embodiments of the disclosure are shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical generator configured to provide high frequency electrosurgical energy at a fundamental frequency, the generator comprising:
   at least one circuit board having a board ground;
   an RF output stage coupled to the at least one circuit board configured to generate sinusoidal waveforms of high frequency electrosurgical energy for at least one electrosurgical mode;
   an alternating current line including a line contact, a neutral contact, and an earth ground contact;
   a DC power supply coupled to the board ground and to the alternating current line, the DC power supply configured to provide high voltage DC current to the RF output stage, the DC power supply having a capacitance and the alternating current line having a capacitance; and
   an inductor-capacitor filter connected in series between the board ground and the earth ground contact of the alternating current line, the inductor-capacitor filter including a capacitor connected in parallel with an inductor, wherein the inductor is tuned to resonate with the capacitor, the capacitance of the alternating current line, and the capacitance of the DC power supply at an operational frequency that is at or near a fundamental frequency of the high frequency electrosurgical energy.

2. An electrosurgical generator as in claim 1, wherein the fundamental frequency is from about 100 kHz to about 3.3 MHz.

3. An electrosurgical generator as in claim 1, wherein the operational frequency is from about 100 kHz to about 3.3 MHz.

4. An electrosurgical generator as in claim 1, wherein the RF output stage is disposed on the at least one circuit board.

5. An electrosurgical circuit board, comprising:
   an RF output stage configured to generate sinusoidal waveforms of high frequency electrosurgical energy at a fundamental frequency for at least one electrosurgical mode;
   a board ground;
   an alternating current line including a line contact, a neutral contact, and an earth ground contact;
   a DC power supply coupled to the board ground and to the alternating current line, the DC power supply configured to provide high voltage DC current to the RF output stage, the DC power supply having a capacitance and the alternating current line having a capacitance; and
   an inductor-capacitor filter connected in series between the board ground and the earth ground contact of the alternating current line, the inductor-capacitor filter including a capacitor connected in parallel with an inductor, wherein the inductor is tuned to resonate with the capacitor, the capacitance of the alternating current line, and the capacitance of the DC power supply at an operational frequency that is at or near a fundamental frequency of the high frequency electrosurgical energy.

6. An electrosurgical circuit board as in claim 5, wherein the fundamental frequency is from about 100 kHz to about 3.3 MHz.

7. An electrosurgical circuit board as in claim 5, wherein the operational frequency is from about 100 kHz to about 3.3 MHz.

8. A method for reducing leakage current in an electrosurgical generator, comprising:
   providing at least one circuit board having a board ground, the at least one circuit board coupled to an RF output stage configured to generate sinusoidal waveforms of high frequency electrosurgical energy for at least one electrosurgical mode and a DC power supply coupled to the board ground and to an alternating current line, the alternating current line including a line contact, a neutral contact, and an earth ground contact, the DC power supply configured to provide high voltage DC current to the RF output stage, the DC power supply having a capacitance and the alternating current line having a capacitance;
   connecting an inductor-capacitor filter in series between the board ground and the earth ground contact of the alternating current line, the inductor-capacitor filter including a capacitor connected in parallel with an inductor; and
   tuning the inductor-capacitor filter to resonate with the capacitor, the capacitance of the alternating current line, and the capacitance of the DC power supply at an operational frequency that is at or near a fundamental frequency of the high frequency electrosurgical energy.

9. A method as in claim 8, wherein the fundamental frequency is from about 100 kHz to about 3.3 MHz.

10. A method as in claim 8, wherein the operational frequency is from about 100 kHz to about 3.3 MHz.

11. A method as in claim 8, wherein the step of providing the at least one circuit board further comprises:
    disposing the RF output stage on the at least one circuit board.

* * * * *